(12) United States Patent
Norman et al.

(10) Patent No.: US 10,964,966 B2
(45) Date of Patent: Mar. 30, 2021

(54) FLOW BATTERIES INCORPORATING A NITROXIDE COMPOUND WITHIN AN AQUEOUS ELECTROLYTE SOLUTION

(71) Applicant: LOCKHEED MARTIN ENERGY, LLC, Bethesda, MD (US)

(72) Inventors: Zachariah M. Norman, Belmont, MA (US); Matthew Millard, Belmont, MA (US); Emily Grace Nelson, Watertown, MA (US); Scott Thomas Humbarger, Somerville, MA (US)

(73) Assignee: Lockheed Martin Energy, LLC, Bethesda, MD (US)

( * ) Notice: Subject to any disclaimer, the term of this patent is extended or adjusted under 35 U.S.C. 154(b) by 53 days.

(21) Appl. No.: 16/469,766

(22) PCT Filed: Dec. 15, 2017

(86) PCT No.: PCT/US2017/066792
§ 371 (c)(1),
(2) Date: Jun. 14, 2019

(87) PCT Pub. No.: WO2018/112396
PCT Pub. Date: Jun. 21, 2018

(65) Prior Publication Data
US 2020/0014054 A1    Jan. 9, 2020

Related U.S. Application Data

(60) Provisional application No. 62/435,376, filed on Dec. 16, 2016.

(51) Int. Cl.
*H01M 4/36*     (2006.01)
*H01M 8/18*     (2006.01)
(Continued)

(52) U.S. Cl.
CPC .......... *H01M 8/188* (2013.01); *C07D 209/04* (2013.01); *C07D 209/46* (2013.01);
(Continued)

(58) Field of Classification Search
CPC ........ H01M 8/188; H01M 8/184; H01M 8/18; H01M 4/368; H01M 4/60; C07D 209/04;
(Continued)

(56) References Cited

U.S. PATENT DOCUMENTS 6,692,862 B1 *   2/2004  Zocchi ................. H01M 8/188
                                                           429/50
2014/0255734 A1 *  9/2014  Tennessen ............ H01M 8/20
                                                           429/51
(Continued)

FOREIGN PATENT DOCUMENTS

JP   2009295881 A   12/2009
JP   2012256505 A   12/2012

*Primary Examiner* — Raymond Alejandro
(74) *Attorney, Agent, or Firm* — BakerHostetler

(57) ABSTRACT

Flow batteries can include a first half-cell containing a first aqueous electrolyte solution, a second half-cell containing a second aqueous electrolyte solution, and a separator disposed between the first half-cell and the second half-cell. The first aqueous electrolyte solution contains a first redox-active material, and the second aqueous electrolyte solution contains a second redox-active material. At least one of the first redox-active material and the second redox-active material is a nitroxide compound or a salt thereof. Particular nitroxide compounds can include a doubly bonded oxygen contained in a ring bearing the nitroxide group, a doubly bonded oxygen appended to a ring bearing the nitroxide group, sulfate or phosphate groups appended to a ring bearing the nitroxide group, various heterocyclic rings bearing the nitroxide group, or acyclic nitroxide compounds.

17 Claims, 1 Drawing Sheet

(51) Int. Cl.
  *C07D 209/04*   (2006.01)
  *C07D 209/46*   (2006.01)
  *C07D 221/00*   (2006.01)
  *C07D 279/12*   (2006.01)
  *C07F 1/00*     (2006.01)
  *C07F 3/00*     (2006.01)
  *H01M 4/60*     (2006.01)

(52) U.S. Cl.
  CPC ......... *C07D 221/00* (2013.01); *C07D 279/12* (2013.01); *C07F 1/005* (2013.01); *C07F 3/003* (2013.01); *H01M 4/368* (2013.01); *H01M 4/60* (2013.01)

(58) Field of Classification Search
  CPC .. C07D 209/10; C07D 209/12; C07D 209/18; C07D 209/46; C07D 209/44; C07D 221/00; C07D 279/12; C07F 1/005; C07F 3/003
  See application file for complete search history.

(56) References Cited

U.S. PATENT DOCUMENTS

2016/0276695 A1    9/2016  Esswein et al.
2017/0317363 A1*  11/2017  Pijpers .............. H01M 8/04276
2018/0294502 A1*  10/2018  Selverston .............. H01M 8/20

\* cited by examiner

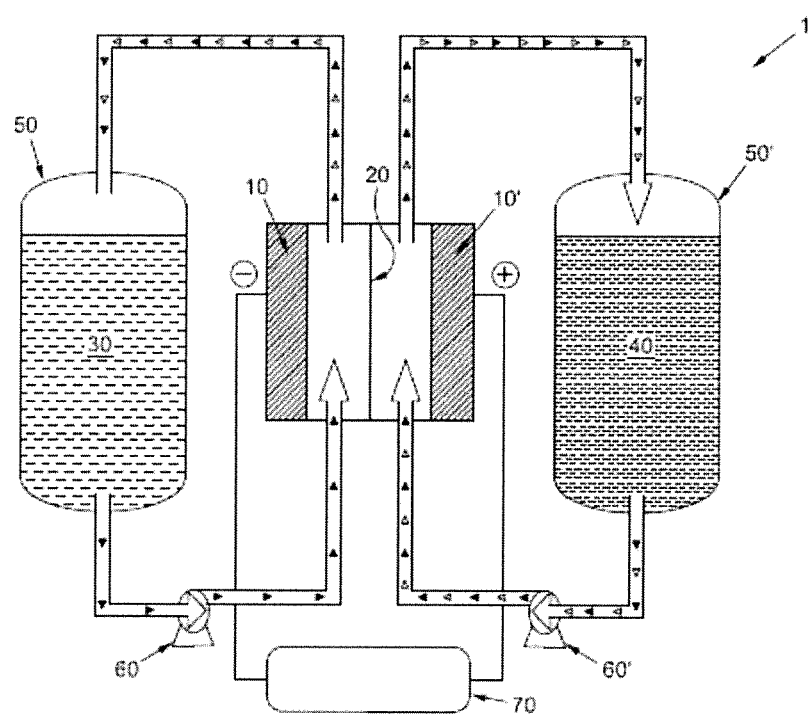

FLOW BATTERIES INCORPORATING A NITROXIDE COMPOUND WITHIN AN AQUEOUS ELECTROLYTE SOLUTION

CROSS-REFERENCE TO RELATED APPLICATIONS

This application is the U.S. National Stage Application of International Patent Application No. PCT/US2017/066792, filed Dec. 15, 2017 which claims priority to U.S. Patent Application No. 62/435,376 filed Dec. 16, 2016, the disclosures of which is are incorporated herein by reference in their entireties.

STATEMENT REGARDING FEDERALLY SPONSORED RESEARCH OR DEVELOPMENT

Not applicable.

FIELD

The present disclosure generally relates to energy storage and, more specifically, to flow batteries and other electrochemical systems containing an organic redox-active material bearing a stabilized radical.

BACKGROUND

Electrochemical energy storage systems, such as batteries, supercapacitors and the like, have been widely proposed for large-scale energy storage applications. Various battery designs, including flow batteries, have been considered for this purpose. Compared to other types of electrochemical energy storage systems, flow batteries can be advantageous, particularly for large-scale applications, due to their ability to decouple the parameters of power density and energy density from one another.

Flow batteries generally include negative and positive active materials in corresponding electrolyte solutions, which are flowed separately across opposing faces of a membrane or separator in an electrochemical cell containing negative and positive electrodes. The terms "membrane" and "separator" are used synonymously herein. The flow battery is charged or discharged through electrochemical reactions of the active materials that occur inside the two half-cells. As used herein, the terms "active material," "electroactive material," "redox-active material" or variants thereof synonymously refer to materials that undergo a change in oxidation state during operation of a flow battery or like electrochemical energy storage system (i.e., during charging or discharging).

Although flow batteries hold significant promise for large-scale energy storage applications, they have historically been plagued by sub-optimal energy storage performance (e.g., round trip energy efficiency) and limited cycle life, among other factors. Despite significant investigational efforts, no commercially viable flow battery technologies have yet been developed.

Numerous classes of active materials have been studied in efforts to improve the performance of flow batteries. Both organic active materials and metal-based active materials have been extensively studied.

Organic compounds that are able to undergo a reversible oxidation-reduction cycle can serve as active materials in a flow battery. Organic active materials can be in one or both of the half-cells. Although organic compounds are often capable of transferring more than one electron during an oxidation-reduction cycle, which can be desirable, their use as active materials has historically proven problematic. In particular, many organic compounds offer relatively limited conductivity and energy density values when utilized as active materials. The low energy density values frequently arise due to the relatively low solubility of organic compounds, particularly in aqueous electrolyte solutions. To compensate for their low solubility values, organic compounds are frequently utilized in non-aqueous electrolyte solutions in which they are more soluble. Excessive costs, potential safety issues, and undesired environmental impacts can sometimes accompany the use of organic solvents, particularly in commercial-scale flow battery systems. For the limited set of organic compounds that possess relatively good aqueous solubility, reversibility of the electrochemical kinetics can often be poor, particularly in alkaline aqueous solutions.

Metal-based active materials can similarly undergo a reversible oxidation-reduction cycle when utilized in at least one half-cell of a flow battery. Metal-based active materials can be present in both half-cells of a flow battery, or they can be used in combination with organic active materials in opposing half-cells. Although non-ligated metal ions (e.g., dissolved salts of a redox-active metal) can be used as an active material, it can often be more desirable to utilize coordination compounds for this purpose. As used herein, the terms "coordination complex, "coordination compound," and "metal-ligand complex" synonymously refer to a compound having at least one covalent bond formed between a metal center and a donor ligand. The donor ligands in a coordination compound can favorably impact solubility as well as tailor the reduction potential of the active material.

Because of their high positive reduction potentials and favorable electrochemical kinetics, iron hexacyanide coordination compounds have historically been a desirable active material for use in the positive half-cell of flow batteries. Although iron hexacyanide coordination compounds are not overly expensive, they still represent one of the more costly components utilized in conventional flow batteries. In addition, the cyanide ligands carried by these coordination compounds can present undesirable environmental, health and safety concerns if not properly managed. In particular, iron hexacyanide coordination compounds can react with certain coordination compounds under some conditions, especially at elevated states of charge, to liberate hydrogen cyanide gas, which is an extreme health hazard.

In view of the foregoing, alternative redox-active materials capable of enhancing the performance and safety of flow batteries would be highly desirable in the art. The present disclosure satisfies the foregoing needs and provides related advantages as well.

SUMMARY

In various embodiments, the present disclosure provides flow batteries including a first half-cell containing a first aqueous electrolyte solution, a second half-cell containing a second aqueous electrolyte solution, and a separator disposed between the first half-cell and the second half-cell. The first aqueous electrolyte solution contains a first redox-active material, and the second aqueous electrolyte solution contains a second redox-active material. At least one of the first redox-active material and the second redox-active material is a nitroxide compound or a salt thereof. In certain embodiments, the nitroxide compound can be a piperidine-based nitroxide compound bearing a doubly bonded oxygen at the 4-position of the piperidine ring [i.e., C(=O), S(=O), S(=O)$_2$ P(=O)R or P(=O)OR, where R is alkyl or aryl]. In certain embodiments, the nitroxide compound can be a piperidine-based nitroxide compound bearing a doubly bonded oxygen appended to the piperidine ring at the 4-position (e.g., ketones, esters, amides, sulfonic acids, sulfones, sulfonamides, ureas, thioureas, phosphonates, and the like). In certain embodiments, the nitroxide compound can be a piperidine-based nitroxide compound bearing a sulfate, phosphate or polyphosphate group appended to the piperidine framework at the 4-position via an oxygen linker. In certain embodiments, the nitroxide compound can be based upon a heterocyclic ring framework that is not a piperidine framework. In certain embodiments, the nitroxide compound can be an acyclic nitroxide compound.

The foregoing has outlined rather broadly the features of the present disclosure in order that the detailed description that follows can be better understood. Additional features and advantages of the disclosure will be described hereinafter. These and other advantages and features will become more apparent from the following description.

BRIEF DESCRIPTION OF THE DRAWINGS

For a more complete understanding of the present disclosure, and the advantages thereof, reference is now made to the following descriptions to be taken in conjunction with the accompanying drawings describing specific embodiments of the disclosure, wherein:

FIG. 1 depicts a schematic of an illustrative flow battery.

DETAILED DESCRIPTION

The present disclosure is directed, in part, to flow batteries incorporating a nitroxide compound or a salt thereof as a redox-active material in an aqueous electrolyte solution, particularly [2,2,6,6-tetramethyl-4-(sulfooxy)piperidin-1-yl]oxidanyl. The present disclosure is also directed, in part, to methods for operating flow batteries containing a nitroxide compound or a salt thereof as a redox-active material in an aqueous electrolyte solution. The present disclosure is also directed, in part, to aqueous solutions containing [2,2,6,6-tetramethyl-4-(sulfooxy)piperidin-1-yl]oxidanyl or a salt thereof and to methods for making [2,2,6,6-tetramethyl-4-(sulfooxy)piperidin-1-yl]oxidanyl.

The present disclosure may be understood more readily by reference to the following description taken in connection with the accompanying FIGURES and examples, all of which form a part of this disclosure. It is to be understood that this disclosure is not limited to the specific products, methods, conditions or parameters described and/or shown herein. Further, the terminology used herein is for purposes of describing particular embodiments by way of example only and is not intended to be limiting unless otherwise specified. Similarly, unless specifically stated otherwise, any description herein directed to a composition is intended to refer to both solid and liquid versions of the composition, including solutions and electrolytes containing the composition, and electrochemical cells, flow batteries, and other energy storage systems containing such solutions and electrolytes. Further, it is to be recognized that where the disclosure herein describes an electrochemical cell, flow battery, or other energy storage system, it is to be appreciated that methods for operating the electrochemical cell, flow battery, or other energy storage system are also implicitly described.

It is also to be appreciated that certain features of the present disclosure may be described herein in the context of separate embodiments for clarity purposes, but may also be provided in combination with one another in a single embodiment. That is, unless obviously incompatible or specifically excluded, each individual embodiment is deemed to be combinable with any other embodiment(s) and the combination is considered to represent another distinct embodiment. Conversely, various features of the present disclosure that are described in the context of a single embodiment for brevity's sake may also be provided separately or in any sub-combination. Finally, while a particular embodiment may be described as part of a series of steps or part of a more general structure, each step or sub-structure may also be considered an independent embodiment in itself.

Unless stated otherwise, it is to be understood that each individual element in a list and every combination of individual elements in that list is to be interpreted as a distinct embodiment. For example, a list of embodiments presented as "A, B, or C" is to be interpreted as including the embodiments "A," "B," "C," "A or B," "A or C," "B or C," or "A, B, or C."

In the present disclosure, the singular forms of the articles "a," "an," and "the" also include the corresponding plural references, and reference to a particular numerical value includes at least that particular value, unless the context clearly indicates otherwise. Thus, for example, reference to "a material" is a reference to at least one of such materials and equivalents thereof.

In general, use of the term "about" indicates approximations that can vary depending on the desired properties sought to be obtained by the disclosed subject matter and is to be interpreted in a context-dependent manner based on functionality. Accordingly, one having ordinary skill in the art will be able to interpret a degree of variance on a case-by-case basis. In some instances, the number of significant FIGURES used when expressing a particular value may be a representative technique of determining the variance permitted by the term "about." In other cases, the gradations in a series of values may be used to determine the range of variance permitted by the term "about." Further, all ranges in the present disclosure are inclusive and combinable, and references to values stated in ranges include every value within that range.

As discussed above, energy storage systems that can be operated on a large scale while maintaining high operating efficiencies and energy densities can be extremely desirable. Flow batteries have generated significant interest in this regard, but there remains room for improving their performance, cost, safety and potential environmental impact. Exemplary description of illustrative flow batteries, their use, and operating characteristics is provided hereinbelow.

The present inventors discovered that certain organic compounds containing stabilized nitroxyl radicals can suitably be used as an active material in aqueous electrolyte solutions. In particular, the inventors discovered several related structural classes of organic compounds that can be suitable for incorporation in aqueous electrolyte solutions. Aqueous electrolyte solutions containing a nitroxide compound can be especially beneficial when incorporated in the positive half-cell of a flow battery due to their high positive half-cell reduction potentials. In addition, at least some of the nitroxide compounds discovered by the inventors display substantially reversible electrochemical kinetics, even in highly alkaline aqueous electrolyte solutions. Reversible electrochemical kinetics in alkaline aqueous electrolyte solutions is considerably rare in the realm of organic active materials. As such, at least some of the nitroxide compounds discovered by the inventors represent a significant advance in the art.

The high positive half-cell reduction potentials can provide significant advantages when incorporated in flow batteries, particularly in comparison to the commonly used iron hexacyanide coordination compounds. The high positive reduction potential can allow improved open circuit potential, voltage efficiency and current efficiency values to be realized. In addition, the improved solubility of many nitroxide compounds compared to iron hexacyanide coordination compounds allows improved energy density values to be realized. Thus, by replacing an iron hexacyanide active material with a nitroxide compound or a salt thereof, significantly improved safety and performance of a flow battery can be realized. The electrochemical kinetics for at least some of the nitroxide compounds identified by the inventors may also be substantially reversible, which can also be advantageous for flow batteries. As used herein, the term "substantially reversible" in regard to electrochemical kinetics means that the voltage difference between the anodic and cathodic peaks is less than about 0.3 V, as measured by cyclic voltammetry. In more particular embodiments, the term "substantially reversible" refers to a voltage difference between anodic and cathodic peaks of less than about 0.1 V or less than about 59 mV, as measured by cyclic voltammetry.

In addition, some of the nitroxide compounds disclosed herein contain a functional group that is capable of bearing a negative charge. Under alkaline aqueous conditions, these functional groups can be deprotonated to expose the negative charge and form a salt form of the nitroxide compound. The negatively charged nitroxide compounds can be especially advantageous, since they are less prone to cross over a membrane or separator into the opposing half-cell. As discussed hereinbelow, negatively charged nitroxide compounds are also thought to contribute to reversibility of the electrochemical kinetics in some instances. Suitable salt forms can include, for example, alkali metals, mixture of alkali metals, ammonium, tetraalkylammonium salt forms, or any mixture thereof.

Finally, some nitroxide compounds bearing ligatable functional groups can be bonded to a metal center in a coordination compound. Coordination of a nitroxide compound to a metal center can also improve aqueous solubility and/or tailor the reduction potential in some instances. In addition, because both the nitroxide compound and the metal center can be redox-active, more electrons can be transferred on a molar basis during an oxidation-reduction cycle than with just the nitroxide compound alone.

Before discussing further specifics of suitable nitroxide compounds and flow batteries incorporating nitroxide compounds, a brief discussion of flow batteries and their operating characteristics will first be provided so that the embodiments of the present disclosure can be better understood.

Unlike typical battery technologies (e.g., Li-ion, Ni-metal hydride, lead-acid, and the like), where redox-active materials and other components, such as electrolyte substances, are housed in a single assembly, flow batteries transport (e.g., via pumping) redox-active materials from receptacles (i.e., storage tanks) through an electrochemical stack containing one or more electrochemical cells. This design feature decouples the electrical energy storage system power from the energy storage capacity, thereby allowing for considerable design flexibility and cost optimization. FIG. 1 shows a schematic of an illustrative flow battery containing a single electrochemical cell. Although FIG. 1 shows a flow battery containing a single electrochemical cell, approaches for combining multiple electrochemical cells together are known and are discussed in brief hereinbelow. Active materials containing nitroxide compounds can be incorporated in these and other types of flow batteries, particularly in the positive half-cell.

As shown in FIG. 1, flow battery 1 includes an electrochemical cell that features separator 20 between electrodes 10 and 10' in corresponding first and second half-cells. As used herein, the terms "separator" and "membrane" synonymously refer to an ionically conductive and electrically insulating material disposed between the positive and negative electrodes of an electrochemical cell. Electrodes 10 and 10' are formed from a suitably conductive material, such as a metal, carbon, graphite, and the like, and the materials for the two can be the same or different. Although FIG. 1 has shown electrodes 10 and 10' as being spaced apart from separator 20, electrodes 10 and 10' can also be abutted with separator 20 in more particular embodiments. The material(s) forming electrodes 10 and 10' can be porous, such that they have a high surface area for contacting first electrolyte solution 30 and second electrolyte solution 40, the active materials of which are capable of cycling between an oxidized state and a reduced state during operation of flow battery 1. For example, one or both of electrodes 10 and 10' can be formed from a porous carbon cloth or a carbon foam in particular embodiments.

Pump 60 affects transport of first electrolyte solution 30 containing a first active material from tank 50 to the electrochemical cell. The flow battery also suitably includes second tank 50' that holds second electrolyte solution 40 containing a second active material. The second active material in second electrolyte solution 40 can be the same material as the first active material in first electrolyte solution 30, or it can be different. More desirably, the first and second active materials differ from one another. In particular, at least one of the first and second active materials is a nitroxide compound according to the present disclosure. Second pump 60' can similarly affect transport of second electrolyte solution 40 to the electrochemical cell. Pumps (not shown in FIG. 1) can also be used to affect transport of first and second electrolyte solutions 30 and 40 from the electrochemical cell back to tanks 50 and 50'. Electrolytes (i.e., mobile ions) in first and second electrolyte solutions 30 and 40 also circulate between the electrochemical cell and tanks 50 and 50' in this process. Other methods of affecting fluid transport, such as siphons, for example, can also suitably transport first and second electrolyte solutions 30 and 40 into and out of the electrochemical cell. Also shown in FIG. 1 is power source or load 70, which completes the circuit of the electrochemical cell and allows a user to collect or store electricity during its operation. Connection to the electrical grid for charging or discharging purposes can also occur at this location.

It should be understood that FIG. 1 depicts a specific, non-limiting configuration of a particular flow battery. Accordingly, flow batteries consistent with the spirit of the present disclosure can differ in various aspects relative to the configuration of FIG. 1. As one example, a flow battery can include one or more active materials that are solids, gases, and/or gases dissolved in liquids. Active materials can be stored in a tank, in a vessel open to the atmosphere, or simply vented to the atmosphere.

During operation of a flow battery in a charging cycle, one of the active materials undergoes oxidation and the other active material undergoes reduction. In a discharging cycle, the opposite processes occur in each half-cell. Upon changing the oxidation states of the active materials, the chemical potentials of the electrolyte solutions are no longer in balance with one another. To relieve the chemical potential imbalance, mobile ions migrate through the separator to lower the charge in one electrolyte solution and to raise the charge in the other electrolyte solution. Thus, the mobile ions transfer the charge generated upon oxidizing or reducing the active materials, but the mobile ions themselves are not oxidized or reduced.

As indicated above, multiple electrochemical cells can also be combined with one another in an electrochemical stack in order to increase the rate that energy can be stored and released during operation. The amount of energy released is determined by the overall amount of active materials that are present. An electrochemical stack utilizes bipolar plates between adjacent electrochemical cells to establish electrical communication but not fluid communication between the two cells across the bipolar plate. Thus, bipolar plates contain the electrolyte solutions in an appropriate half-cell within the individual electrochemical cells. Bipolar plates are generally fabricated from electrically conductive materials that are fluidically non-conductive on the whole. Suitable materials can include carbon, graphite, metal, certain metal oxides, or a combination thereof. Bipolar plates can also be fabricated from non-conducting polymers having a conductive material dispersed therein, such as carbon particles or fibers, metal particles or fibers, graphene, and/or carbon nanotubes. Although bipolar plates can be fabricated from some of the same types of conductive materials as can the electrodes of an electrochemical cell, they can lack the continuous porosity permitting an electrolyte solution to flow completely through the latter. It should be recognized that bipolar plates are not necessarily entirely non-porous entities, however. Bipolar plates can have innate or designed flow channels that provide a greater surface area for allowing an electrolyte solution to contact the bipolar plate. Suitable flow channel configurations can include, for example, interdigitated flow channels. In some embodiments, the flow channels can be used to promote delivery of an electrolyte solution to an electrode within the electrochemical cell.

In some instances, an electrolyte solution can be delivered to and withdrawn from each electrochemical cell via a fluid inlet manifold and a fluid outlet manifold (not shown in FIG. 1). In some embodiments, the fluid inlet manifold and the fluid outlet manifold can provide and withdraw an electrolyte solution via the bipolar plates separating adjacent electrochemical cells. Separate manifolds can provide each electrolyte solution individually to the two half-cells of each electrochemical cell. In more particular embodiments, the fluid inlet manifold and the fluid outlet manifold can be configured to supply and withdraw the electrolyte solutions via opposing lateral faces of the bipolar plates (e.g. by supplying and withdrawing the electrolyte solution from opposing ends of the flow channels of the bipolar plate).

Accordingly, in various embodiments, the present disclosure provides flow batteries including a first half-cell containing a first aqueous electrolyte solution, a second half-cell containing a second aqueous electrolyte solution, and a separator disposed between the first half-cell and the second half-cell. The first aqueous electrolyte solution contains a first redox-active material, and the second aqueous electrolyte solution contains a second redox-active material. At least one of the first redox-active material and the second redox-active material is a nitroxide compound or a salt thereof. In certain embodiments, the nitroxide compound can be a pyrrolidine-based nitroxide compound bearing a doubly bonded oxygen at the 4-position of the pyrrolidine ring [i.e., C(=O), S(=O), S(=O)$_2$ P(=O)R or P(=O)OR, where R is alkyl or aryl, and the oxygen is doubly bonded to the heteroatom in the ring]. In certain embodiments, the nitroxide compound can be a pyrrolidine-based nitroxide compound bearing a doubly bonded oxygen appended to the pyrrolidine ring at the 4-position (e.g., ketones, esters, amides, sulfonic acids, sulfones, sulfates, sulfonamides, ureas, thioureas, phosphonates, phosphates, polyphosphates, and the like, where these groups are not part of the pyrrolidine ring). In certain embodiments, the nitroxide compound can be based upon heterocyclic ring framework that is not a pyrrolidine framework. In certain embodiments, the nitroxide compound can be an acyclic nitroxide compound. Particular examples are discussed in more detail below.

In some embodiments, the nitroxide compounds suitable for use in the present disclosure can have Structure 1 or a salt thereof, which are based upon a functionalized piperidine framework.

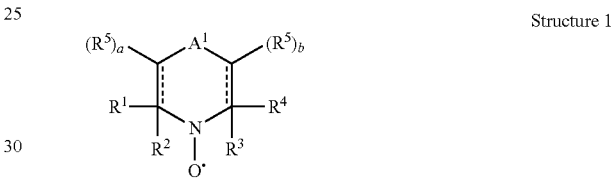

Structure 1

$R^1$-$R^4$ are independently selected from the group consisting of $C_1$-$C_{10}$ straight chain or branched alkyl, any of which can be optionally substituted. Each $R^5$ is independently selected from the group consisting of H; optionally substituted alkyl, alkenyl, alkynyl, aryl, aralkyl, heterocyclyl, or heteroaryl; $C_2$-$C_6$ polyol; C(=O)$R^6$; C(=O)O$R^6$; C(=O)N$R^6R^6$; O$R^6$; O(C=O)$R^6$; S$R^6$; S(=O)$R^6$; S(=O)$_2R^6$; N$R^6R^6$; N$R^6$(C=O)$R^6$; N$R^6$(C=O)N$R^6R^6$; (CH$_2$)$_{1-10}$CO$_2$H; (CH$_2$)$_{1-10}$(CHOH)CO$_2$H; CH$_2$(OCH$_2$CH$_2$)$_x$OCH$_3$; CH$_2$(OCH$_2$CH$_2$)$_x$OCH$_3$; CH(OH)CH$_2$OH; halogen; cyano; sulfonyl; and perfluoroalkyl. Each $R^6$ is independently selected from the group consisting of consisting of H; optionally substituted alkyl, alkenyl, alkynyl, aryl, aralkyl, heterocyclyl, or heteroaryl; perfluoroalkyl; (CH$_2$)$_{1-10}$CO$_2$H; (CH$_2$)$_{1-10}$(CHOH)CO$_2$H; (CH$_2$CH$_2$O)CH$_3$; CH$_2$(OCH$_2$CH$_2$)OCH$_3$; CH(OH)CH$_2$OH; and $C_2$-$C_6$ polyol. The dashed lines represent optional double bonds in the six-membered ring. Depending upon whether double bonds are present, variables a and b can be either 1 or 2. Variable x is an integer ranging between 0 and about 100.

Referring still to Structure 1, $A^1$ can be selected from the group consisting of C(=O), S(=O), S(=O)$_2$, P(=O)$R^7$, and P(=O)O$R^7$. $R^7$ is an optionally substituted alkyl or aryl group. Each of these nitroxide compounds incorporate an oxygen atom that is doubly bonded to the piperidine framework to a heteroatom therein. In at least some instances, the doubly bonded oxygen atom may contribute to stabilization of the nitroxide compound.

In more specific embodiments, suitable nitroxide compounds related to Structure 1 can have Structure 2 or a salt thereof, wherein only single bonds are present within piperidine framework, and the variables are otherwise defined as above.

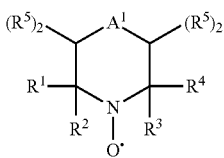

Structure 2

In more specific embodiments of Structure 2, each $R^5$ is H. In some or other embodiments, $R^1$-$R^4$ are each methyl. As such, more particular examples of suitable nitroxide compounds are shown in Structure 3.

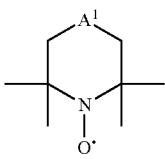

Structure 3

Still more particular examples of suitable nitroxide compounds related to Structures 1-3 include those wherein $A^1$ is selected from the group consisting of $S(=O)$, $S(=O)_2$, $P(=O)R^7$, and $P(=O)OR^7$.

In still more particular embodiments, a suitable nitroxide compound related to Structures 1-3 is defined by Structure 4, in which $A^1$ is $S(=O)$. The sulfoxide group is considered to be in resonance with Structure 5.

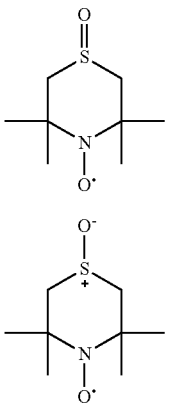

Structure 4

Structure 5

In some or other embodiments, suitable nitroxide compounds for incorporation in flow batteries can be defined by Structure 6 or a salt thereof.

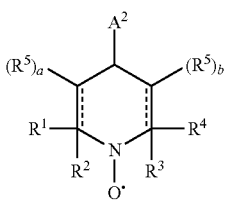

Structure 6

In Structure 6, $R^1$-$R^5$, a and b are defined as above. In the case of Structure 6, $A^2$ is selected from the group consisting of $C(=O)R^8$, $C(=O)OR^8$, $C(=O)NR^9R^9$, $NR^9C(=O)R^9$, $S(=O)OH$, $S(=O)R^8$, $S(=O)_2R^8$, $S(=O)_2NR^9R^9$, $OS(=O)_2OR^{10}$, $NR^9C(=O)NR^9R^9$, $NR^9C(=S)NR^9R^9$, $NR^9S(=O)_2R^8$, $P(=O)(OR^9)_2$, $P(=O)R^8OR^9$, $P(=O)R^8$, $PR^9$, $OP(=O)OR^{10}$, and $OP(=O)OP(=O)OR^{10}$. The groups defining $A^2$ in Structure 6 can desirably place a doubly bonded oxygen atom in a similar location within the nitroxide compound as those defined by Structures 1-5. $R^8$ is selected from the group consisting of optionally substituted alkyl, alkenyl, alkynyl, aryl, aralkyl, heterocyclyl, or heteroaryl; perfluoroalkyl; $(CH_2)_{1-10}CO_2H$; $(CH_2)_{1-10}(CHOH)CO_2H$; $(CH_2CH_2O)_xCH_3$; $CH_2(OCH_2CH_2)_xOCH_3$; $CH(OH)CH_2OH$; and $C_2$-$C_6$ polyol. $R^9$ is selected from the group consisting of H; optionally substituted alkyl, alkenyl, alkynyl, aryl, aralkyl, heterocyclyl, or heteroaryl; perfluoroalkyl; $(CH_2)_{1-10}CO_2H$; $(CH_2)_{1-10}(CHOH)CO_2H$; $(CH_2CH_2O)_xCH_3$; $CH_2(OCH_2CH_2)_xOCH_3$; $CH(OH)CH_2OH$; and $C_2$-$C_6$ polyol.

In some embodiments, $R^{10}$ is selected from the group consisting of H; optionally substituted alkyl, alkenyl, alkynyl, aryl, aralkyl, heterocyclyl, or heteroaryl; perfluoroalkyl; $(CH_2)_{1-10}CO_2H$; $(CH_2)_{1-10}(CHOH)CO_2H$; $(CH_2CH_2O)_xCH_3$; $CH_2(OCH_2CH_2)_xOCH_3$; $CH(OH)CH_2OH$; and $C_2$-$C_6$ polyol. In more specific embodiments, $R^{10}$ is selected from the group consisting of H, alkyl and aryl. In some embodiments, $R^{10}$ is H, in which case the nitroxide compound can be in a suitable salt form, if desired.

In more specific embodiments, suitable nitroxide compounds related to Structure 6 can have Structure 7, wherein only single bonds are present within the piperidine framework, wherein the variables are otherwise defined as above.

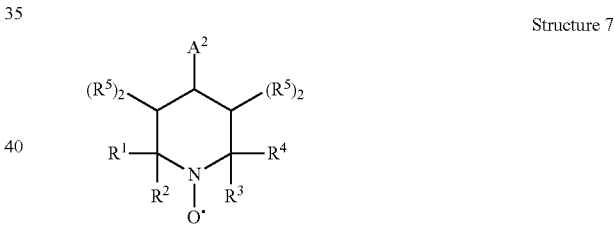

Structure 7

In more specific embodiments of Structure 7, each $R^5$ is H. In some or other embodiments, $R^1$-$R^4$ are each methyl. As such, more particular examples of suitable nitroxide compounds are shown in Structure 8.

Structure 8

Still more particular examples of suitable nitroxide compounds related to Structures 6-8 include those wherein $A^2$ is selected from the group consisting of $S(=O)OH$, $S(=O)R^8$, $S(=O)_2R^8$, $S(=O)_2NR^9R^9$, $OS(=O)_2OR^{10}$, $NR^9C(=O)R^9$, $NR^9C(=O)NR^9R^9$, $NR^9C(=S)NR^9R^9$, and $NR^9S(=O)_2R^8$. Each $R^9$, when present, can be selected independently of one another in a given nitroxide compound.

Still more particular examples of suitable nitroxide compounds related to Structures 6-8 include those wherein $A^2$ is selected form the group consisting of $S(=O)_2NR^9R^9$, $NR^9S(=O)_2R^8$, and $OS(=O)_2OR^{10}$ These compounds are shown in Structures 9-11.

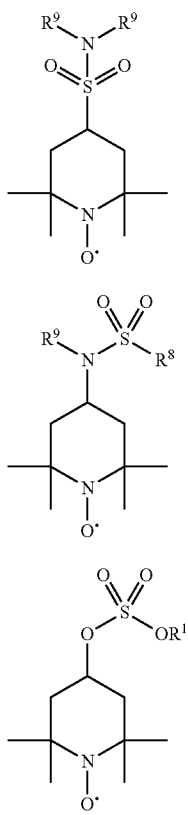

Structure 9

Structure 10

Structure 11

In Structure 9, in the case where one of $R^9$ is H and the other $R^9$ is not H (i.e., each $R^9$ is independently selected), the NH group is acidic and can potentially stabilize the nitroxide group when forming a salt form. Similarly, in Structure 10, in the case where $R^9$ is H, the NH group is acidic and can deprotonate to form a salt form.

In still more particular embodiments, the nitroxide compound defined by Structure 11 can have Structure 12, wherein $R^{10}$ is H.

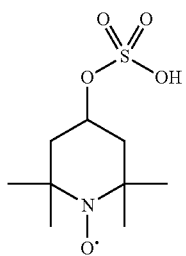

Structure 12

Like Structures 9 and 10, the acidic hydrogen of Structure 12 can deprotonate and form a salt form. Suitable salt forms for the nitroxide compound of Structure 12 include, for example, an alkali metal salt (e.g., Li, Na, K, Rb, Cs, or any combination thereof), an ammonium salt, or tetraalkylammonium salt form.

The nitroxide compound defined by Structure 12 has the chemical name [2,2,6,6-tetramethyl-4-(sulfooxy)piperidin-1-yl]oxidanyl (also referred to herein as TEMPOSO). Without being bound by any theory or mechanism, it is believed that the sulfate (sulfooxy) group can stabilize the nitroxide group when the six-membered ring is in its "boat" configuration. TEMPOSO can particularly be desirable for use in flow batteries due to its ability to maintain substantially reversible electrochemical kinetics even in alkaline aqueous electrolyte solutions. Under alkaline aqueous solutions, the deprotonated anionic form of Structure 12 can be stabilized after oxidation of the radical through lone pair donation from the sulfooxy group to the resulting nitrogen-centered cation. Remaining unbound by theory or mechanism, it is believed that the negatively charged oxygen atom of the anionic form of Structure 12 can be particularly facile at stabilizing the nitroxide group and for promoting substantially reversible electrochemical kinetics.

As mentioned above, TEMPOSO displays substantially reversible electrochemical kinetics. In addition to this desirable feature, this compound also displays a number of other desirable properties. First, it has a reduction potential of approximately 0.6 V versus a saturated calomel electrode, which is desirably higher than that of iron hexacyanide coordination compounds (increase of 0.25 V). In addition, it has an aqueous solubility of at least approximately 1.8 M, which is again desirably higher than that of iron hexacyanide coordination compounds and their maximum aqueous solubility of about 1.5 M. In particular embodiments, the aqueous solubility can range between about 1.5 M and about 8 M, or between about 1.5 M and about 3 M. In a 1 M aqueous solution, TEMPOSO has a conductivity of about 50 mS/cm at pH 11, even in the absence of other electrolytes. Finally, TEMPOSO can be readily synthesized from acetone, ammonia, and sulfur trioxide, which are low-cost starting materials, and the cost of this material is believed to be at least comparable or superior to that of iron hexacyanide compounds.

In other illustrative embodiments, TEMPOSO can be synthesized from 2,2,6,6-tetramethyl-1-($\lambda^1$-oxidanyl)piperidin-4-ol (4-OH-TEMPO). In brief, chlorosulfonic acid can be added to 4-OH-TEMPO in an ice-cooled solution of dichloromethane, and the reaction mixture can thereafter be treated with aqueous sodium hydroxide solution. The resulting aqueous layer can be concentrated to afford crude product, which can then be crystallized from acetone.

In some or other embodiments, suitable nitroxide compounds for incorporation in flow batteries can include those having a framework other than that defined by a piperidine derivative. In illustrative embodiments, suitable nitroxide compounds can include those having a pyrroline, pyrrolidine, imidazoline, imidazolidine, oxazoline, oxazolidine, thiazoline, thioazolidine, and their benzo-fused analogues. Similarly, indolines and isoindolines can constitute the framework for suitable nitroxide compounds in some embodiments. Illustrative nitroxide compounds based upon a heterocyclic framework other than a piperidine framework include, but are not limited to, those shown in Structures 13-20 below.

Structure 13

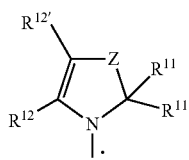

Structure 14

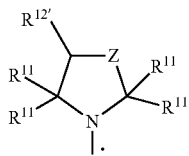

Structure 15

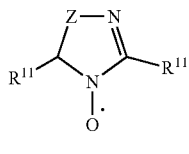

Structure 16

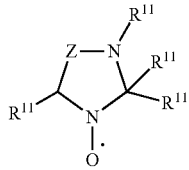

Structure 17

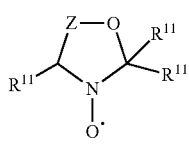

Structure 18

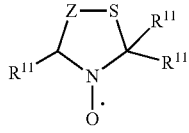

Structure 19

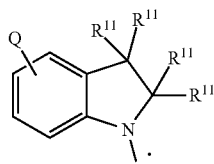

Structure 20

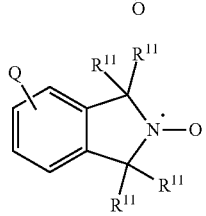

In Structures 13-20, $R^{11}$ is H or $R^1$, and each $R^{11}$ is selected independently of one another. $R^{12}$ and $R^{12'}$ are H or $R^1$, or are linked to one another in an optionally substituted aromatic, heteroaromatic, or heterocyclic ring. In Structures 19 and 20, Q represents optional substitution upon the aromatic ring.

In still other embodiments, suitable nitroxide compounds for inclusion in a flow battery can include those based upon an azabicycloheptane framework.

In still other alternative embodiments, suitable nitroxide compounds for inclusion in a flow battery can include acyclic nitroxide compounds such as di-t-butylnitroxide.

As used herein, the term "alkyl" refers to a straight-chain, branched or cyclic carbon chain containing 1 to about 16 carbon atoms and no carbon-carbon unsaturation. As used herein, the term "carbon-carbon unsaturation" refers to a carbon-carbon double bond or triple bond.

As used herein, the term "alkenyl" refers to a straight-chain, branched or cyclic carbon chain containing 2 to about 16 carbon atoms and at least one carbon-carbon double bond. The at least one carbon-carbon double bond can be in any location in the carbon chain and in either the E or Z configuration.

As used herein, the term "alkynyl" refers to a straight-chain, branched or cyclic carbon chain containing 2 to about 16 carbon atoms and at least one carbon-carbon triple bond. The at least one carbon-carbon triple bond can be in any location in the carbon chain.

As used herein, the term "aryl" refers to a monocyclic or polycyclic aromatic group containing 6 to about 19 carbon atoms.

As used herein, the term "heteroaryl" refers to a monocylic or polycyclic aromatic group containing 5 to about 18 carbon atoms and at least one heteroatom within at least one of the aromatic groups. More specifically, the at least one heteroatom in a heteroaryl group can be O, N or S.

As used herein, the term "heterocyclyl" refers to a monocyclic or polycyclic group containing 3 to about 10 carbon atoms that is non-aromatic and contains at least one heteroatom within at least one ring.

As used herein, the term "aralkyl" refers an alkyl group in which at least one hydrogen atom has been replaced by an aryl or heteroaryl group.

As used herein, the term "polyol" refers to any compound having two or more alcohol functional groups. Additional heteroatom functionality, such as amines and carboxylic acids, can optionally be present within a polyol. Thus, amino alcohol and hydroxy acid analogues of unmodified glycols and higher polyols are also encompassed by the term "polyol." Any of the alcohol, amine and/or carboxylic acid functional groups can be used to form a bond to the nitroxide compound. Some illustrative polyols can include monosaccharides. As used herein, term "monosaccharide" refers to both the base monosaccharide and the corresponding sugar alcohols, sugar acids, and deoxy sugars of the base monosaccharide, including any open- or closed-chain forms of these materials. Illustrative polyols include, for example, 1,2-ethanediol (ethylene glycol), 1,2-propanediol (propylene glycol), 1,3-propanediol, 1,2-butanediol, 1,4-butanediol, glycerol, erythritol, threitol, arabitol, xylitol, ribitol, mannitol, sorbitol, galacitol, fucitol, iditol, inositol, glycolaldehyde, glyceraldehyde, 1,3-dihydroxyacetone, erythrose, threose, erythrulose, arabinose, ribose, lyxose, xylose, ribulose, xylulose, allose, altrose, glucose, mannose, gulose, idose, galactose, talose, psicose, fructose, sorbose, tagatose, deoxyribose, rhamnose, fucose, glyceric acid, xylonic acid, gluconic acid, ascorbic acid, glucuronic acid, galacturonic acid, iduronic acid, tartartic acid, galactaric acid, and glucaric acid.

As used herein, the term "perfluoroalkyl" refers to an alkyl group that has at least 50% of its hydrogen atoms replaced by fluoro groups. In some embodiments, at least about 90% of the hydrogen atoms are replaced by fluoro groups, and in some embodiments, all of the hydrogen atoms are replaced by fluoro groups.

As used herein, the term "optionally substituted" refers to an alkyl, alkenyl, alkynyl, aryl, aralkyl, heterocyclyl, or heteroaryl group being either unsubstituted or bearing at least one heteroatom substituent. As used herein, the term "heteroatom substituent" refers to a functional group containing one or more O, N or S atoms, or a halogen atom. As used herein, the term "halogen" refers to F, Cl, Br or I. Illustrative heteroatom substituents that can optionally be present include, but are not limited to, hydroxyl, alkoxy, cyano, nitro, carboxyl, carboxamide, carboxylic ester, carbonyl, amine, ether, sulfonyl, fluoro, chloro, bromo, iodo, and trihaloalkyl. In the case of a carbon chain, the at least one heteroatom substituent can either be appended from the carbon chain and/or replace one or more of the carbon atoms within the carbon chain. In the case of a heterocyclic or heteroaromatic ring, the at least one heteroatom substituent can be appended from the heterocyclic or heteroaromatic ring.

In some embodiments, the first redox-active material or the second redox-active material can be an unbound form of the nitroxide compound. In other embodiments, the first redox-active material or the second redox-active material can be a coordination compound containing the nitroxide compound. When present as a ligand, suitable functionality for complexing or chelating a metal center can be present upon the nitroxide compound. In some embodiments, the metal center of a coordination compound in which a nitroxide compound ligand is present can be a titanium metal center.

In some more specific embodiments, only one of the first aqueous electrolyte solution and the second aqueous electrolyte solution contains the nitroxide compound. Again, the nitroxide compound can be in a free form or an unbound form.

In more particular embodiments, the nitroxide compound can be present in the first aqueous electrolyte solution. In still more particular embodiments, the first aqueous electrolyte solution can be present in the first half-cell of the flow battery, where the first half-cell is a positive half-cell. As such, the nitroxide compound can constitute the positive active material in the flow battery and replace other positive active materials, such as iron hexacyanide coordination compounds.

In further embodiments, in which the nitroxide compound is present in a positive half-cell of the flow battery, the second half-cell can be a negative half-cell of the flow battery and contain a second redox-active material that is a coordination compound. Suitable coordination compounds for the second redox-active material can include those described hereinafter. Particularly suitable coordination compounds for use as the second redox-active material can be titanium coordination compounds, although other coordination compounds containing other metals can also be utilized.

in some embodiments, coordination compounds suitable for use as the second redox-active material can have a formula of

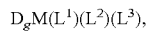

$$D_gM(L^1)(L^2)(L^3),$$

wherein M is a transition metal, lanthanide metal or main group metal, more particularly a transition metal; D is ammonium, tetraalkylammonium ($C_1$-$C_4$ alkyl), an alkali metal ion (e.g., Li$^+$, Na$^+$ and/or K$^+$), or any combination thereof; g ranges between 0 and 6; and $L^1$, $L^2$ and $L^3$ are ligands. In some embodiments, at least one of $L^1$, $L^2$ and $L^3$ can be a catecholate ligand or substituted catecholate ligand, and in other embodiments, each of $L^1$, $L^2$ and $L^3$ can be a catecholate ligand or substituted catecholate ligand. Suitable substituted catecholate ligand can include, for example, monosulfonated catecholate ligands, hydroxylated catecholate ligands, or carboxylated catecholate ligands. In general, any of the 4 open valences on the phenyl ring of the catecholate ligands can be optionally substituted, and the substitution(s) can be the same or different on each phenyl ring when multiple catecholate ligands are present. Optional substitutions can include, for example, $C_{1-6}$ alkoxy, $C_{1-6}$ alkyl, $C_{1-6}$ alkenyl, $C_{1-6}$ alkynyl, 5- or 6-membered aryl or heteroaryl groups, a boronic acid or a derivative thereof, a carboxylic acid or a derivative thereof, cyano, halide, hydroxyl, nitro, sulfonate, a sulfonic acid or a derivative thereof, a phosphonate, a phosphonic acid or a derivative thereof, or a glycol, such as polyethylene glycol, any of which, if chemically feasible, can be further substituted. Catecholate ligands can be especially desirable to include in a coordination compound serving as an active material in a flow battery due to the relatively good aqueous solubility of these groups, their ready complexation of metals, and their contribution to a high negative half-cell potential when present.

When less than all the open coordination sites are filled in the coordination compounds, one or more additional ligands can be present. Suitable additional ligands that can be present include, for example, an unsubstituted catecholate, a substituted catecholate, ascorbate, citrate, glycolate, a polyol, gluconate, hydroxyalkanoate, acetate, formate, benzoate, malate, maleate, phthalate, sarcosinate, salicylate, oxalate, urea, polyamine, aminophenolate, acetylacetonate, and lactate. Where chemically feasible, it is to be recognized that these ligands can be optionally substituted with at least one group selected from among $C_{1-6}$ alkoxy, $C_{1-6}$ alkyl, $C_{1-6}$ alkenyl, $C_{1-6}$ alkynyl, 5- or 6-membered aryl or heteroaryl groups, a boronic acid or a derivative thereof, a carboxylic acid or a derivative thereof, cyano, halide, hydroxyl, nitro, sulfonate, a sulfonic acid or a derivative thereof, a phosphonate, a phosphonic acid or a derivative thereof, or a glycol, such as polyethylene glycol, any of which, if chemically feasible, can be further substituted. Where feasible, neighboring substituents can form or be bonded to alicyclic, aromatic, heteroaromatic or heterocyclic rings that can optionally be further substituted. Alkanoate includes any of the alpha, beta, and gamma forms of these ligands. Polyamines include, but are not limited to, ethylenediamine, ethylenediamine tetraacetic acid (EDTA), and diethylenetriamine pentaacetic acid (DTPA). Still other examples of additional ligands that can be present include, for example, carbonyl or carbon monoxide, nitride, oxo, hydroxo, water, sulfide, thiols, pyridine, pyrazine, bipyridine, bipyrazine, ethylenediamine, diols (including ethylene glycol), terpyridine, diethylenetriamine, triazacyclononane, tris(hydroxymethyl)aminomethane, and the like. These additional ligands can, where chemically feasible, bear any of the optional substitutions discussed above. Where feasible, neighboring substituents can form or be bonded to alicyclic, aromatic, heteroaromatic or heterocyclic rings that can optionally be further substituted. Monocyclic, polycyclic and/or fused ring systems can be produced.

Due to their variable oxidation states, transition metals (Groups 3-12 of the periodic table plus Al) can be highly desirable for incorporation within the second redox-active material of the flow batteries described herein. Lanthanide elements can be used similarly in this regard. In general, any transition metal or lanthanide metal can be present as the metal center in the coordination compounds of the present disclosure. Main group metals can also be used similarly in this regard, in some embodiments. In more specific embodiments, the metal center can be a transition metal selected from among Al, Cr, Ti and Fe. For purposes of the present disclosure, Al is to be considered a transition metal. In more specific embodiments, the transition metal can be Ti. Other suitable transition and main group metals that can be present in the coordination compounds of the present disclosure include, for example, Ca, Ce, Co, Cu, Mg, Mn, Mo, Ni, Pb, Pd, Pt, Ru, Sb, Sr, Sn, V, Zn, Zr, and any combination thereof. In various embodiments, the coordination compounds can include a transition metal in a non-zero oxidation state when the transition metal is in both its oxidized and reduced forms. Cr, Fe, Mn, Ti and V can be particularly desirable in this regard.

The aqueous electrolyte solutions of the present disclosure, in which the nitroxide compound or salt thereof is present, will now be discussed in further detail.

As used herein, the term "aqueous electrolyte solution" refers to a homogeneous liquid phase with water as a predominant solvent in which an active material is solubilized. This definition encompasses both solutions in water and solutions containing a water-miscible organic solvent as a minority component of an aqueous phase.

Illustrative water-miscible organic solvents that can be present in an aqueous electrolyte solution of the present disclosure include, for example, alcohols and glycols, optionally in the presence of one or more surfactants or other components discussed below. In more specific embodiments, an aqueous electrolyte solution can contain at least about 98% water by weight. In other more specific embodiments, an aqueous electrolyte solution can contain at least about 55% water by weight, or at least about 60% water by weight, or at least about 65% water by weight, or at least about 70% water by weight, or at least about 75% water by weight, or at least about 80% water by weight, or at least about 85% water by weight, or at least about 90% water by weight, or at least about 95% water by weight. In some embodiments, an aqueous electrolyte solution of the present disclosure can be free of water-miscible organic solvents and consist of water alone as a solvent.

In further embodiments, an aqueous electrolyte solution of the present disclosure can include a viscosity modifier, a wetting agent, or any combination thereof. Suitable viscosity modifiers can include, for example, corn starch, corn syrup, gelatin, glycerol, guar gum, pectin, and the like. Other suitable examples will be familiar to one having ordinary skill in the art. Suitable wetting agents can include, for example, various non-ionic surfactants and/or detergents. In some or other embodiments, an aqueous electrolyte solution can further include a glycol or a polyol. Suitable glycols can include, for example, ethylene glycol, diethylene glycol, and polyethylene glycol. Suitable polyols can include, for example, glycerol, mannitol, sorbitol, pentaerythritol, and tris(hydroxymethyl)aminomethane. Inclusion of any of these components in an aqueous electrolyte solution of the present disclosure can help promote dissolution of a nitroxide compound or a coordination compound and/or reduce viscosity of the aqueous electrolyte solution for conveyance through a flow battery, for example.

In some embodiments, an aqueous electrolyte solution in which a nitroxide compound is present can have an acidic pH. In more particular embodiments, the pH can range between about 1 and about 6, or between about 4 and about 6.5, or between about 3 and about 6, or between about 2 and about 5. In other embodiments, an aqueous electrolyte solution in which a nitroxide compound is present can have an alkaline pH. Illustrative alkaline pH values can range between 8 and about 14, or between about 12 and about 14, or between about 9 and about 12, or between about 7.5 and about 11. As discussed above, an alkaline pH aqueous electrolyte solution can desirably promote formation of a salt form of the nitroxide compound in some instances.

In some or other illustrative embodiments, an aqueous electrolyte solution in which a coordination compound is present can have an alkaline pH. Alkaline pH values can be especially suitable for maintaining stability of coordination compounds containing catecholate ligands, for example. In more particular embodiments, the pH can range between about 8 and about 14, or between about 12 and about 14, or between about 9 and about 12, or between about 7.5 and about 11. In alternative embodiments, an aqueous electrolyte solution in which a coordination compound is present can have an acidic pH, including the acid pH ranges discussed above for the aqueous electrolyte solution in which the nitroxide compound is present.

In certain embodiments, the first aqueous electrolyte solution can have an acidic pH, and the second aqueous electrolyte solution can have an alkaline pH. In other embodiments, the pH of both aqueous electrolyte solutions can be chosen such that they are each acidic or each alkaline. In some embodiments, the pH of both aqueous electrolyte solutions can be within about 2 pH units of each other.

In addition to a solvent and a redox-active material, the aqueous electrolyte solutions can also include one or more mobile ions. In some embodiments, suitable mobile ions can include proton, hydronium, or hydroxide. In other various embodiments, mobile ions other than proton, hydronium, or hydroxide can be present, either alone or in combination with proton, hydronium or hydroxide. Such alternative mobile ions can include, for example, alkali metal or alkaline earth metal cations (e.g., $Li^+$, $Na^+$, $K^+$, $Mg^{2+}$, $Ca^{2+}$ and $Sr^{2+}$) and halides (e.g., F+, $Cl^-$, or BO. In some embodiments, alkali metal halides can be particularly suitable salts for supplying the mobile ions. Other suitable mobile ions can include, for example, ammonium and tetraalkylammonium ions, chalcogenides, phosphate, hydrogen phosphate, phosphonate, nitrate, sulfate, nitrite, sulfite, perchlorate, tetrafluoroborate, hexafluorophosphate, and any combination thereof. In some embodiments, less than about 50% of the mobile ions can constitute protons, hydronium, or hydroxide. In other various embodiments, less than about 40%, less than about 30%, less than about 20%, less than about 10%, less than about 5%, or less than about 2% of the mobile ions can constitute protons, hydronium, or hydroxide.

In various embodiments, a concentration of the redox-active material in an aqueous electrolyte solution can range between about 0.1 M and about 3 M. This concentration range represents the sum of the individual concentrations of the oxidized and reduced forms of the redox-active material. In more particular embodiments, the concentration of the redox-active material can range between about 0.5 M and about 3 M, or between 1 M and about 3 M, or between about 1.5 M and about 3 M, or between 1 M and about 2.5 M.

Illustrative flow battery configurations and methods that can incorporate the foregoing aqueous electrolyte solutions will now be described in further detail. The flow batteries of the present disclosure are, in some embodiments, suited to sustained charge or discharge cycles of several hour durations. As such, they can be used to smooth energy supply/demand profiles and provide a mechanism for stabilizing intermittent power generation assets (e.g., from renewable energy sources such as solar and wind energy). It should be appreciated, then, that various embodiments of the present disclosure include energy storage applications where such long charge or discharge durations are desirable. For example, in non-limiting examples, the flow batteries of the present disclosure can be connected to an electrical grid to allow renewables integration, peak load shifting, grid firming, baseload power generation and consumption, energy arbitrage, transmission and distribution asset deferral, weak grid support, frequency regulation, or any combination thereof. When not connected to an electrical grid, the flow batteries of the present disclosure can be used as power sources for remote camps, forward operating bases, off-grid telecommunications, remote sensors, the like, and any combination thereof. Further, while the disclosure herein is generally directed to flow batteries, it is to be appreciated that other electrochemical energy storage media can incorporate the electrolyte solutions and coordination compounds described herein, specifically those utilizing stationary electrolyte solutions.

In some embodiments, flow batteries of the present disclosure can include: a first chamber containing a positive electrode contacting a first aqueous electrolyte solution; a second chamber containing a negative electrode contacting a second aqueous electrolyte solution, and a separator disposed between the first and second electrolytes solutions. The chambers provide separate reservoirs within the cell, through which the first and/or second aqueous electrolyte solutions circulate so as to contact the respective electrodes and the separator. Each chamber and its associated electrode and electrolyte solution define a corresponding half-cell. The separator provides several functions which include, for example, (1) serving as a barrier to mixing of the first and second electrolyte solutions, (2) electrically insulating to reduce or prevent short circuits between the positive and negative electrodes, and (3) to facilitate ion transport between the positive and negative electrolyte chambers, thereby balancing electron transport during charge and discharge cycles. The negative and positive electrodes provide a surface where electrochemical reactions can take place during charge and discharge cycles; During a charge or discharge cycle, electrolyte solutions can be transported from separate storage tanks through the corresponding chambers. The mobile ions of the electrolyte solutions remain continuously soluble during this process. In a charging cycle, electrical power can be applied to the electrochemical cell such that the redox-active material contained in the second electrolyte solution undergoes a one or more electron oxidation and the redox-active material in the first electrolyte solution undergoes a one or more electron reduction. Similarly, in a discharge cycle the second redox-active material is reduced and the first redox-active material is oxidized to generate electrical power.

In more specific embodiments, illustrative flow batteries of the present disclosure can include: (a) a first aqueous electrolyte solution containing a first redox-active material; (b) a second aqueous electrolyte solution containing a second redox-active material; (c) a separator positioned between said first and second aqueous electrolyte solutions; and (d) mobile ions in the first and second aqueous electrolyte solutions. As described in more detail below, the separator can be an ionomer membrane, and it can have a thickness of less than 100 microns. In some embodiments, an ionomer membrane can have an associated net charge that is the same sign as that of the first and second redox-active materials.

Polymer membranes can be anion- or cation-conducting electrolytes. Where described as an "ionomer," the term refers to polymer membrane containing both electrically neutral repeating units and ionized repeating units, where the ionized repeating units are pendant and covalently bonded to the polymer backbone. In general, the fraction of ionized units can range from about 1 mole percent to about 90 mole percent. For example, in some embodiments, the content of ionized units is less than about 15 mole percent; and in other embodiments, the ionic content is higher, such as greater than about 80 mole percent. In still other embodiments, the ionic content is defined by an intermediate range, for example, in a range of about 15 to about 80 mole percent. Ionized repeating units in an ionomer can include anionic functional groups such as sulfonate, carboxylate, and the like. These functional groups can be charge balanced by, mono-, di-, or higher-valent cations, such as alkali or alkaline earth metals. Ionomers can also include polymer compositions containing attached or embedded quaternary ammonium, sulfonium, phosphazenium, and guanidinium residues or salts. Suitable examples will be familiar to one having ordinary skill in the art.

In some embodiments, polymers useful as a separator can include highly fluorinated or perfluorinated polymer backbones. Certain polymers useful in the present disclosure can include copolymers of tetrafluoroethylene and one or more fluorinated, acid-functional co-monomers, which are commercially available as NAFION™ perfluorinated polymer electrolytes from DuPont. Other useful perfluorinated polymers can include copolymers of tetrafluoroethylene and $FSO_2$—$CF_2CF_2CF_2CF_2$—O—$CF$=$CF_2$, FLEMION™ and SELEMION™.

Additionally, substantially non-fluorinated membranes that are modified with sulfonic acid groups (or cation exchanged sulfonate groups) can also be used. Such membranes can include those with substantially aromatic backbones such as, for example, polystyrene, polyphenylene, biphenyl sulfone (BPSH), or thermoplastics such as polyetherketones and polyethersulfones.

Battery-separator style porous membranes, can also be used as the separator. Because they contain no inherent ionic conduction capabilities, such membranes are typically impregnated with additives in order to function. These membranes typically contain a mixture of a polymer and inorganic filler, and open porosity. Suitable polymers can include, for example, high density polyethylene, polypropylene, polyvinylidene difluoride (PVDF), or polytetrafluoroethylene (PTFE). Suitable inorganic fillers can include silicon carbide matrix material, titanium dioxide, silicon dioxide, zinc phosphide, and ceria.

Separators can also be formed from polyesters, polyetherketones, poly(vinyl chloride), vinyl polymers, and substituted vinyl polymers. These can be used alone or in combination with any previously described polymer.

Porous separators are non-conductive membranes which allow charge transfer between two electrodes via open channels filled with electrolyte. The permeability increases the probability of chemicals (e.g., redox-active materials) passing through the separator from one electrode to another and causing cross-contamination and/or reduction in cell energy efficiency. The degree of this cross-contamination can depend on, among other features, the size (the effective diameter and channel length), and character (hydrophobicity/hydrophilicity) of the pores, the nature of the electrolyte, and the degree of wetting between the pores and the electrolyte.

The pore size distribution of a porous separator is generally sufficient to substantially prevent the crossover of redox-active materials between the two electrolyte solutions. Suitable porous membranes can have an average pore size distribution of between about 0.001 nm and 20 micrometers, more typically between about 0.001 nm and 100 nm. The size distribution of the pores in the porous membrane can be substantial. In other words, a porous membrane can contain a first plurality of pores with a very small diameter (approximately less than 1 nm) and a second plurality of pores with a very large diameter (approximately greater than 10 micrometers). The larger pore sizes can lead to a higher amount of active material crossover. The ability for a porous membrane to substantially prevent the crossover of active materials can depend on the relative difference in size between the average pore size and the active material. For example, when the active material is a metal center in a coordination compound, the average diameter of the coordination compound can be about 50% greater than the average pore size of the porous membrane. On the other hand, if a porous membrane has substantially uniform pore sizes, the average diameter of the coordination compound can be about 20% larger than the average pore size of the porous membrane. Likewise, the average diameter of a coordination compound is increased when it is further coordinated with at least one water molecule. The diameter of a coordination compound of at least one water molecule is generally considered to be the hydrodynamic diameter. In such embodiments, the hydrodynamic diameter is generally at least about 35% greater than the average pore size. When the average pore size is substantially uniform, the hydrodynamic radius can be about 10% greater than the average pore size.

In some embodiments, the separator can also include reinforcement materials for greater stability. Suitable reinforcement materials can include nylon, cotton, polyesters, crystalline silica, crystalline titania, amorphous silica, amorphous titania, rubber, asbestos, wood or any combination thereof.

Separators within the flow batteries of the present disclosure can have a membrane thickness of less than about 500 micrometers, or less than about 300 micrometers, or less than about 250 micrometers, or less than about 200 micrometers, or less than about 100 micrometers, or less than about 75 micrometers, or less than about 50 micrometers, or less than about 30 micrometers, or less than about 25 micrometers, or less than about 20 micrometers, or less than about 15 micrometers, or less than about 10 micrometers. Suitable separators can include those in which the flow battery is capable of operating with a current efficiency of greater than about 85% with a current density of 100 mA/cm$^2$ when the separator has a thickness of 100 micrometers. In further embodiments, the flow battery is capable of operating at a current efficiency of greater than 99.5% when the separator has a thickness of less than about 50 micrometers, a current efficiency of greater than 99% when the separator has a thickness of less than about 25 micrometers, and a current efficiency of greater than 98% when the separator has a thickness of less than about 10 micrometers. Accordingly, suitable separators include those in which the flow battery is capable of operating at a voltage efficiency of greater than 60% with a current density of 100 mA/cm$^2$. In further embodiments, suitable separators can include those in which the flow battery is capable of operating at a voltage efficiency of greater than 70%, greater than 80% or even greater than 90%.

The diffusion rate of the first and second redox-active materials through the separator can be less than about $1 \times 10^{-5}$ mol cm$^{-2}$ day$^{-1}$, or less than about $1 \times 10^{-6}$ mol cm$^{-2}$ day$^{-1}$, or less than about $1 \times 10^{-7}$ mol cm$^{-2}$ day$^{-1}$, or less than about $1 \times 10^{-9}$ mol cm$^{-2}$ day$^{-1}$, or less than about $1 \times 10^{-11}$ mol cm$^{-2}$ day$^{-1}$, or less than about $1 \times 10^{-13}$ mol cm$^{-2}$ day$^{-1}$, or less than about $1 \times 10^{-15}$ mol cm$^{-2}$ day$^{-1}$.

The flow batteries can also include an external electrical circuit in electrical communication with the first and second electrodes. The circuit can charge and discharge the flow battery during operation. Reference to the sign of the net ionic charge of the first, second, or both redox-active materials relates to the sign of the net ionic charge in both oxidized and reduced forms of the redox-active materials under the conditions of the operating flow battery. Further exemplary embodiments of a flow battery provide that (a) the first redox-active material has an associated net positive or negative charge and is capable of providing an oxidized or reduced form over an electric potential in a range of the negative operating potential of the system, such that the resulting oxidized or reduced form of the first redox-active material has the same charge sign (positive or negative) as the first redox-active material and the ionomer membrane also has a net ionic charge of the same sign; and (b) the second redox-active material has an associated net positive or negative charge and is capable of providing an oxidized or reduced form over an electric potential in a range of the positive operating potential of the system, such that the resulting oxidized or reduced form of the second redox-active material has the same charge sign (positive or negative sign) as the second redox-active material and the ionomer membrane also has a net ionic charge of the same sign; or both (a) and (b). The matching charges of the first and/or second redox-active materials and the ionomer membrane can provide a high selectivity. More specifically, charge matching can provide less than about 3%, less than about 2%, less than about 1%, less than about 0.5%, less than about 0.2%, or less than about 0.1% of the molar flux of ions passing through the ionomer membrane as being attributable to the first or second redox-active material. The term "molar flux of ions" will refer to the amount of ions passing through the ionomer membrane, balancing the charge associated with the flow of external electricity/electrons. That is, the flow battery is capable of operating or operates with the exclusion or substantial exclusion of the active materials by the ionomer membrane through judicious charge matching.

Flow batteries incorporating the electrolyte solutions of the present disclosure can have one or more of the following operating characteristics: (a) where, during the operation of the flow battery, the first or second redox-active materials comprise less than about 3% of the molar flux of ions passing through the ionomer membrane; (b) where, the round trip current efficiency is greater than about 70%, greater than about 80%, or greater than about 90%; (c) where the round trip current efficiency is greater than about 90%; (d) where the sign of the net ionic charge of the first, second, or both redox-active materials is the same in both oxidized and reduced forms of the redox-active materials and matches that of the ionomer membrane; (e) where the ionomer membrane has a thickness of less than about 100 µm, less than about 75 µm, less than about 50 µm, or less than about 250 µm; (f) where the flow battery is capable of operating at a current density of greater than about 100 mA/cm$^2$ with a round trip voltage efficiency of greater than about 60%; and (g) where the energy density of the electrolyte solutions is greater than about 10 Wh/L, greater than about 20 Wh/L, or greater than about 30 Wh/L.

In some cases, a user may desire to provide higher charge or discharge voltages than are available from a single electrochemical cell. In such cases, several electrochemical cells can be connected in series such that the voltage of each cell is additive. This forms a bipolar stack. An electrically conductive, but non-porous material (e.g., a bipolar plate)

can be employed to connect adjacent battery cells in a bipolar stack, which allows for electron transport but prevents fluid or gas transport between adjacent cells. The positive electrode compartments and negative electrode compartments of individual cells can be fluidically connected via common positive and negative fluid distribution manifolds in the stack. In this way, individual cells can be stacked in series to yield a voltage appropriate for DC applications or conversion to AC applications.

In additional embodiments, the cells, cell stacks, or batteries can be incorporated into larger energy storage systems, suitably including piping and controls useful for operation of these large units. Piping, control, and other equipment suitable for such systems are known in the art, and can include, for example, piping and pumps in fluid communication with the respective chambers for moving electrolyte solutions into and out of the respective chambers and storage tanks for holding charged and discharged electrolytes. The cells, cell stacks, and batteries of this disclosure can also include an operation management system. The operation management system can be any suitable controller device, such as a computer or microprocessor, and can contain logic circuitry that sets operation of any of the various valves, pumps, circulation loops, and the like.

In more specific embodiments, a flow battery system can include a flow battery (including a cell or cell stack); storage tanks and piping for containing and transporting the electrolyte solutions; control hardware and software (which may include safety systems); and a power conditioning unit. The flow battery cell stack accomplishes the conversion of charging and discharging cycles and determines the peak power. The storage tanks contain the positive and negative active materials, and the tank volume determines the quantity of energy stored in the system. The control software, hardware, and optional safety systems suitably include sensors, mitigation equipment and other electronic/hardware controls and safeguards to ensure safe, autonomous, and efficient operation of the flow battery system. A power conditioning unit can be used at the front end of the energy storage system to convert incoming and outgoing power to a voltage and current that is optimal for the energy storage system or the application. For the example of an energy storage system connected to an electrical grid, in a charging cycle the power conditioning unit can convert incoming AC electricity into DC electricity at an appropriate voltage and current for the cell stack. In a discharging cycle, the stack produces DC electrical power and the power conditioning unit converts it to AC electrical power at the appropriate voltage and frequency for grid applications.

Where not otherwise defined hereinabove or understood by one having ordinary skill in the art, the definitions in the following paragraphs are applicable to the present disclosure.

As used herein, the term "energy density" refers to the amount of energy that can be stored, per unit volume, in the active materials. Energy density refers to the theoretical energy density of energy storage and can be calculated by Equation 1:

$$\text{Energy density} = (26.8 \text{ A-h/mol}) \times OCV \times [e^-] \quad \text{(Equation 1)}$$

where OCV is the open circuit potential at 50% state of charge (i.e., the difference in reduction potentials under the condition of the cell), (26.8 A–h/mol) is Faraday's constant, and $[e^-]$ is the concentration of electrons stored in the active material at 99% state of charge. In the case that the active materials largely are an atomic or molecular species for both the positive and negative electrolyte, $[e^-]$ can be calculated by Equation 2 as:

$$[e^-] = [\text{active materials}] \times N/2 \quad \text{(Equation 2)}$$

where [active materials] is the molar concentration of the active material in either the negative or positive electrolyte, whichever is lower, and N is the number of electrons transferred per molecule of active material. The related term "charge density" refers to the total amount of charge that each electrolyte contains. For a given electrolyte, the charge density can be calculated by Equation 3

$$\text{Charge density} = (26.8 \text{ A-h/mol}) \times [\text{active material}] \times N \quad \text{(Equation 3)}$$

where [active material] and N are as defined above.

As used herein, the term "current density" refers to the total current passed in an electrochemical cell divided by the geometric area of the electrodes of the cell and is commonly reported in units of mA/cm².

As used herein, the term "current efficiency" ($I_{eff}$) can be described as the ratio of the total charge produced upon discharge of a cell to the total charge passed during charging. The current efficiency can be a function of the state of charge of the flow battery. In some non-limiting embodiments, the current efficiency can be evaluated over a state of charge range of about 35% to about 60%.

As used herein, the term "voltage efficiency" can be described as the ratio of the observed electrode potential, at a given current density, to the half-cell potential for that electrode (×100%). Voltage efficiencies can be described for a battery charging step, a discharging step, or a "round trip voltage efficiency." The round trip voltage efficiency ($V_{eff,RT}$) at a given current density can be calculated from the cell voltage at discharge ($V_{discharge}$) and the voltage at charge ($V_{charge}$) using Equation 4:

$$V_{eff,RT} = V_{discharge}/V_{charge} \times 100\% \quad \text{(Equation 4)}$$

As used herein, the terms "negative electrode" and "positive electrode" are electrodes defined with respect to one another, such that the negative electrode operates or is designed or intended to operate at a potential more negative than the positive electrode (and vice versa), independent of the actual potentials at which they operate, in both charging and discharging cycles. The negative electrode may or may not actually operate or be designed or intended to operate at a negative potential relative to a reversible hydrogen electrode. The positive electrode is associated with a first electrolyte solution and the negative electrode is associated with a second electrolyte solution, as described herein. The electrolyte solutions associated with the negative and positive electrodes may be described as negolytes and posolytes, respectively.

Although the disclosure has been described with reference to the disclosed embodiments, those skilled in the art will readily appreciate that these are only illustrative of the disclosure. It should be understood that various modifications can be made without departing from the spirit of the disclosure. The disclosure can be modified to incorporate any number of variations, alterations, substitutions or equivalent arrangements not heretofore described, but which are commensurate with the spirit and scope of the disclosure. Additionally, while various embodiments of the disclosure have been described, it is to be understood that aspects of the disclosure may include only some of the described embodiments. Accordingly, the disclosure is not to be seen as limited by the foregoing description.

What is claimed is the following:

1. A flow battery comprising:
   a first half-cell containing a first aqueous electrolyte solution;
   a second half-cell containing a second aqueous electrolyte solution; and
   a separator disposed between the first half-cell and the second half-cell;
   wherein at least one of the first redox-active material and the second redox-active material comprises a nitroxide compound having a structure of:

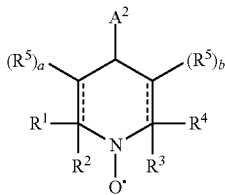

or a salt form thereof;
wherein:
   $R^1$-$R^4$ are, independently, optionally substituted $C_1$-$C_{10}$ straight chain or branched alkyl;
   each $R^5$ is, independently, H; optionally substituted alkyl, alkenyl, alkynyl, aryl, aralkyl, heterocyclyl, or heteroaryl; $C_1$-$C_6$ polyol; C(=O)$R^6$; C(=O)O$R^6$; C(=O)N$R^6R^6$; O$R^6$; O(C=O)$R^6$; S$R^6$; S(=O)$R^6$; S(=O)$_2$$R^6$; N$R^6R^6$; $NR^6$(C=O)$R^6$; $NR^6$(C=O)N$R^6R^6$; $(CH_2)_{1-10}CO_2H$; $(CH_2)_{1-10}(CHOH)CO_2H$; $CH_2(OCH_2CH_2)_xOCH_3$; CH(OH)CH$_2$OH; halogen; cyano; sulfonyl; or perfluoroalkyl;
   each $R^6$ is, independently, H; optionally substituted alkyl, alkenyl, alkynyl, aryl, aralkyl, heterocyclyl, or heteroaryl; perfluoroalkyl; $(CH_2)_{1-10}CO_2H$; $(CH_2)_{1-10}(CHOH)CO_2H$; $(CH_2CH_2O)_xCH_3$; $CH_2(OCH_2CH_2)_xOCH_3$; CH(OH)CH$_2$OH; or $C_2$-$C_6$ polyol;
   optional double bonds are present;
   a and b are, independently, 1 or 2; and
   x is an integer in a range between 0 and about 100;
   $A^2$ is C(=O)$R^8$, C(=O)O$R^8$, C(=O)N$R^9R^9$, $NR^9$C(=O)$R^9$, S(=O)OH, S(=O)$R^8$, S(=O)$_2R^8$, S(=O)$_2$N$R^9R^9$, OS(=O)$_2$O$R^{10}$, $NR^9$C(=O)N$R^9R^9$, $NR^9$C(=S)N$R^9R^9$, $NR^9$S(=O)$_2R^8$, P(=O)(O$R^9$)$_2$, P(=O)$R^8$O$R^9$, P(=O)$R^8$, OP(=O)O$R^{10}$ or P$R^9$;
   $R^8$ is optionally substituted alkyl, alkenyl, alkynyl, aryl, aralkyl, heterocyclyl, or heteroaryl; perfluoroalkyl; $(CH_2)_{1-10}CO_2H$; $(CH_2)_{1-10}(CHOH)CO_2H$; $(CH_2CH_2O)_xCH_3$; $CH_2(OCH_2CH_2)_xOCH_3$; CH(OH)CH$_2$OH; or $C_1$-$C_6$ polyol;
   $R^9$ is H; optionally substituted alkyl, alkenyl, alkynyl, aryl, aralkyl, heterocyclyl, or heteroaryl; perfluoroalkyl; $(CH_2)_{1-10}CO_2H$; $(CH_2)_{1-10}(CHOH)CO_2H$; $(CH_2CH_2O)_xCH_3$; $CH_2(OCH_2CH_2)_xOCH_3$; CH(OH)CH$_2$OH; or $C_2$-$C_6$ polyol; and wherein $R^{10}$ is H; optionally substituted alkyl, alkenyl, alkynyl, aryl, aralkyl, heterocyclyl, or heteroaryl; perfluoroalkyl; $(CH_2)_{1-10}CO_2H$; $(CH_2)_{1-10}(CHOH)CO_2H$; $(CH_2CH_2O)_xCH_3$; $CH_2(OCH_2CH_2)_xOCH_3$; CH(OH)CH$_2$OH; or $C_2$-$C_6$ polyol.

2. The flow battery of claim 1, wherein each $R^5$ is H, and $R^1$-$R^4$ are each methyl.

3. The flow battery of claim 1, wherein $A^2$ is S(=O)OH, S(=O)$R^8$, S(=O)$_2R^8$, S(=O)$_2$N$R^9R^9$, OS(=O)O$R^{10}$, $NR^9$C(=O)N$R^9R^9$, $NR^9$C(=S)N$R^9R^9$, or $NR^9$S(=O)$_2R^8$.

4. The flow battery of claim 3, wherein $A^2$ is S(=O)$_2$N$R^9R^9$ or $NR^9$C(=S)N$R^9R^9$, and at least one $R^9$ bound to N is H.

5. The flow battery of claim 3, wherein $A^2$ is OS(=O)O$R^{10}$.

6. The flow battery of claim 5, wherein $R^{10}$ is H.

7. The flow battery of claim 1, wherein the nitroxide compound is present in only the first aqueous electrolyte solution.

8. The flow battery of claim 7, wherein the first aqueous electrolyte solution is a positive electrolyte solution and the first half-cell is a positive half-cell of the flow battery.

9. The flow battery of claim 8, wherein the second half cell is a negative half-cell of the flow battery, and the second redox-active material is a coordination compound.

10. The flow battery of claim 9, wherein the coordination compound comprises a titanium coordination compound.

11. The flow battery of claim 9, wherein the coordination compound has a formula of:

$$D_gM(L^1)(L^2)(L^3)$$

wherein:
   M is a transition metal or main group metal;
   D is ammonium, tetraalkylammonium, an alkali metal ion, or any combination thereof;
   g is an integer in a range between 0 and 6; and
   $L^1$, $L^2$ and $L^3$ are ligands.

12. The flow battery of claim 11, wherein the transition metal is titanium.

13. The flow battery of claim 11, wherein at least one of $L^1$, $L^2$ and $L^3$ is a catecholate ligand or a substituted catecholate ligand.

14. The flow battery of claim 1, wherein the salt form is an alkali metal salt form, a combination of alkali metal salt forms, an ammonium salt form, a tetraalkylammonium salt form, or any combination thereof.

15. The flow battery of claim 1, wherein $A^2$ is —OS(=O)$_2$O$R^{10}$ or a salt thereof.

16. The flow battery of claim 1, wherein the nitroxide compound is [2,2,6,6,-tetramethyl-4-(sulfooxy)piperidin-1-yl]oxidanyl or a salt thereof.

17. The flow battery of claim 15, wherein the nitroxide compound is an alkali metal, ammonium, or tetraalkylammonium salt of [2,2,6,6,-tetramethyl-4-(sulfooxy)piperidin-1-yl]oxidanyl.

* * * * *